United States Patent
Sekine et al.

[11] Patent Number: 6,104,481
[45] Date of Patent: Aug. 15, 2000

[54] SURFACE INSPECTION APPARATUS

[75] Inventors: Akihiko Sekine; Yoichiro Iwa; Hiroaki Soma; Naoto Miki; Hisashi Isozaki; Hisakazu Yoshino, all of Tokyo, Japan

[73] Assignee: Kabushiki Kaisha Topcon, Tokyo, Japan

[21] Appl. No.: 09/184,075

[22] Filed: Nov. 2, 1998

[30] Foreign Application Priority Data

Nov. 11, 1997 [JP] Japan .................................. 9-323939
Dec. 2, 1997 [JP] Japan .................................. 9-345736

[51] Int. Cl.[7] .................................................. G01N 21/00
[52] U.S. Cl. .................................... 356/237.5; 356/237.4; 356/237.2
[58] Field of Search .............................. 356/237.4, 237.5, 356/239.7, 239.8, 237.3

[56] References Cited

U.S. PATENT DOCUMENTS

| | | | |
|---|---|---|---|
| 4,966,457 | 10/1990 | Hayano et al. ....................... | 356/239.7 |
| 5,179,422 | 1/1993 | Peterson ................................ | 356/237.1 |
| 5,410,400 | 4/1995 | Shishido et al. ....................... | 356/237.4 |
| 5,486,919 | 1/1996 | Tsuji et al. ............................ | 356/237.4 |

*Primary Examiner*—Frank G. Font
*Assistant Examiner*—Zandra V. Smith
*Attorney, Agent, or Firm*—Foley & Lardner

[57] ABSTRACT

A wafer surface inspection apparatus comprises a light source, an optical system for focusing the light beams from the light source onto the wafer surface, a scanning means for scanning the focused point over a predetermined range on the wafer surface, a photo detector including an photoelectric converter for sensing scattered light from the focused point, and a signal detector for detecting signals from the photo detector, in which the light source is a light source for emitting two different wavelengths, the optical system is adapted to focus the light beams of the two wavelengths on one and the same point on the wafer surface, and the photo detector is adapted to sense the two wavelengths separately, and further comprises a discriminating portion for discriminating between a foreign matter or a scratch on the wafer surface and a recess in a spot form existing on the wafer surface by utilizing outputs from the signal detector.

12 Claims, 12 Drawing Sheets

SURFACE INSPECTION APPARATUS

BACKGROUND OF THE INVENTION

The invention generally relates to a surface inspection apparatus of various bodies and, more particularly, relates to a wafer surface inspection apparatus for inspecting foreign matters (such as particles) or scratch (such as crystalline defects) present on the surface of a thin plate type body such as a semiconductor wafer.

RELATED ART

There have so far been known apparatuses throwing light beams on the surface of the inspected body from different angles for each of different inspected bodies and sensing the scattered light from the surface, thereby inspecting foreign matters and the like present on the surface of the inspected body.

For example, there is a defect inspecting apparatus disclosed in Japanese Patent Laid-Open No. 56-67739 using, as the light beams, a plurality of coherent light beams cast on the object from different directions.

In Japanese Patent Laid-Open No. 1-59522, there is disclosed an apparatus for detecting foreign matters on a wafer in which it is adapted such that polarized laser beams are thrown onto a point to be inspected, obliquely from above, in four directions around the inspected point, and specific polarized components are extracted from the reflected light beams from the inspected point and, thereby, foreign matters existing on the wafer on which a circuit pattern is formed is detected.

When a semiconductor wafer is thought of as the inspected body, foreign matters (generally, in the form of a projection) and crystalline defects (generally in the form of a recess) existing on the semiconductor wafer are considered as the objects of inspection.

Further, there are preferred angles of irradiation depending on the kinds of the inspected objects. Hence, it is desired that the inspection be carried out in view of this fact, under suitable conditions for each of the inspected objects, and at the same time for all the objects.

However, the prior art surface inspection apparatuses have been unable to carry out simultaneous inspection of foreign matters (generally, in a projecting form) and crystalline defects (generally, in a recessed form).

A prior art foreign matter inspecting apparatus will be described as related to that for a semiconductor integrated circuit. They are fabricated by forming circuits on a wafer of a semiconductor substrate through the process of photolithography. At this time, a large number of the same integrated circuits are formed on the surface of the wafer and, at last, these are separated into individual integrated circuit chips.

When there is a foreign matter or flaw present at a specific point on the surface of the wafer, the circuit pattern formed at this point becomes defective and the integrated circuit becomes unusable. As a result, the number of integrated circuits obtainable from one wafer decreases and the yield rate falls.

Therefore, it is practiced, prior to the lithographic processing, to inspect the wafer as the material of the semiconductor integrated circuits to thereby ensure that there is no foreign matter present thereon.

As a general method of the inspection, there is such that focuses laser beams on the wafer surface, senses the scattered light from the focused point, and detects a foreign matter or the like on the basis of the signals of the sensed light beams.

In the meantime, miniaturization of circuit patterns has been advanced with the increase in the degree of integration of integrated circuits, and, therefore, the size of the foreign matters to be inspected has become smaller and, accordingly, the sensitivity of the inspection apparatus has been improved.

It has been made known in recent years that what detected as foreign matters by such inspection include by mistake minute recesses in the form of a spot which will not present any problem in the fabrication of circuit patterns.

Because such recesses not presenting any problem in the fabrication of integrated circuits have been mistaken for foreign matters, it has sometimes occurred that a usable wafer is judged defective. Since the recesses have of course been unremovable by rewashing, the wafer has at last been judged to be an unusable wafer and wastefully rejected. This means that the waste will become greater according as the wafers become larger in the future.

SUMMARY OF THE INVENTION

An object of the present invention is to provide a surface inspection apparatus capable of inspecting foreign matters and crystalline defects existing on the surface of the inspected body at the same time and with precision.

Another object of the invention is to provide an inspection method and apparatus which is capable, at the time of surface inspection of a wafer of a semiconductor substrate or the like, of detecting foreign matters or scratch existing on the surface of the wafer and recesses in the form of a spot existing on the surface of the wafer with distinction made between them.

The surface inspection apparatus according to the invention is adapted to throw light beams on an inspected body in different angles of irradiation and sense scattered light from the surface in different angles at the same time. It is thereby made possible to inspect projecting foreign matters and recessed crystalline defects at the same time.

For example, the surface inspection apparatus according to the invention comprises a light source portion emitting a beam of a first wavelength and a beam of a second wavelength, a first illuminating optical system throwing the beam of the first wavelength onto the surface of an inspected body in a first angle of irradiation, a second illuminating optical system throwing the beam of the second wavelength onto the surface of the inspected body in a second angle of irradiation different from the first angle of irradiation, a first photosensing optical system for sensing in a first photosensing direction scattered light from an inspected object on the surface of the inspected body irradiated by the first illuminating optical system, a second photosensing optical system for sensing in a second photosensing direction scattered light from an inspected object on the surface of the inspected body irradiated by the second illuminating optical system, a first photo detector for converting the scattered light of the first wavelength sensed by the first photosensing optical system into a first sensed-light signal, a second photo detector for converting the scattered light of the second wavelength sensed by the first photosensing optical system into a second sensed-light signal, a third photo detector for converting the scattered light of the first wavelength sensed by the second photosensing optical system into a third sensed-light signal, a fourth photo detector for converting the scattered light of the second wavelength sensed by the second photosensing optical system into a fourth sensed-light signal, a displacement portion for producing relative displacement between the inspected body and the beams emitted from the illuminating optical systems, and a signal processing portion for discriminating inspected objects on the basis of the first to fourth sensed-light signals.

In this case, preferably, the first angle of irradiation of the first illuminating optical system is set smaller than the second angle of irradiation of the second illuminating optical system. A first photosensing angle formed between the first photosensing direction, in which the first photosensing optical system senses light, and the direction of the regular reflection of the light beam, which is thrown by the first illuminating optical system or the second illuminating optical system, reflected from the surface of the inspected body is set larger than a second photosensing angle formed between the second photosensing optical system and the direction of the regular reflection. The signal processing portion forms a first processed signal on the basis of the first sensed-light signal or the third sensed-light signal and forms a second processed signal on the basis of the second sensed-light signal or the fourth sensed-light signal and, thereupon, identifies, as the inspected object, a first inspected object by the data included in both of the first processed signal and the second processed signal and a second inspected object by the data included in only one of the first processed signal and the second processed signal.

Preferably, there is provided a sensitivity setting means which is capable of changing over the sensitivity of each of the first to fourth photo detectors to a high sensitivity or a low sensitivity. The sensitivity setting means, when the inspected body is such that produces small surface scattering, sets the first photo detector and the second photo detector at the high sensitivity and sets the third photo detector and the fourth photo detector at the low sensitivity. Further, the sensitivity setting means, when the inspected body is such that produces great surface scattering, sets the first photo detector and the second photo detector at the low sensitivity and sets the third photo detector and the fourth photo detector at the high sensitivity.

It will be assumed that the inspected body is a bare semiconductor wafer. The signal processing portion identifies a foreign matter on the surface of the semiconductor wafer as the first object of inspection and identifies a small recess on the surface of the semiconductor wafer as the second object of inspection. Further, a display portion is provided for displaying one or both of the foreign matter on the surface of the semiconductor wafer as the first object of inspection and the small recess on the surface of the semiconductor wafer as the second object of inspection.

Further, a storage portion for storing the results identified by the signal processing portion is provided and the signal processing portion, when the object of inspection already inspected is inspected again, associates the identified results already stored in the storage portion with the identified results currently measured.

In one of the methods of the invention, a beam of light from the light source is focused on the surface of a wafer and scattered light from the focused point is sensed by a photoelectric converter, while the focused point is being scanned, and a signal from the photoelectric converter is detected, and thereby a foreign matter or a scratch on the surface of the wafer is inspected. Light beams of two different wavelengths are focused on the same point in different angles of incidence and scattered light from the focused point are photoelectrically converted into signals separately for the two wavelengths and, by utilizing the difference in intensity of the signals, a foreign matter or a scratch on the surface of the wafer and a recess in the form of a spot existing on the surface of the wafer are distinguished from each other.

One of the apparatuses carrying out the above described method comprises a light source, an optical system for focusing the light beam from the light source on the surface of a wafer, scanning means for scanning the focused point over a specific region on the surface of the wafer, a photo detector including a photoelectric converter for sensing scattered light from the focused point, and a signal detector for detecting a signal from the photo detector. The light source is such that emits two different wavelengths. The optical system is configured so as to focus beams of two wavelengths on the same point on the surface of the wafer in different angles of incidence. Further, the photo detector is configured so as to sense two wavelengths separately and there is provided a discriminating portion which, by utilizing outputs from the signal detector, discriminates between a foreign matter or a scratch on the surface of the wafer and a recess in the form of a spot existing on the surface of the wafer.

The invention can be applied to wafers used in various technical fields. For example, it can inspect the surface of wafers of a semiconductor substrate and the like.

It is known that the intensity of the scattered light reflected from a foreign matter or the like attached to the surface of a wafer or a scratch formed on the surface of a wafer depends on the relationship between the wavelength of the light beam from the light source and the size of the foreign matter or the flaw and also depends on the angle of incidence and the photosensing orientation and angle. Namely, the intensity of the scattered light varies with the wavelength of the light beam, the size of the foreign matter or the like, the angle of incidence of the light beam, and the photosensing orientation and angle.

For example, while a recess on the surface of a wafer in the form of a spot is sometimes mistaken for a foreign matter, as described above, it is a phenomenon occurring in the range of considerably smaller wavelengths than the wavelengths of the visible region, where the recess produces scattered light at the equal level to that produced by a foreign matter. In such a range, when the orientation and the angle of the photo detector are fixed, the change in intensity of the scattered light against the change in the angle of incidence is greater with a minute recess on the surface than with a foreign matter attached to the surface of the wafer. Then, according as the angle of incidence is made larger, i.e., according as the angle of incidence is brought closer to the inspected surface, with the sensitivity adjusted such that the scattered light from the foreign matter will not be changed, the scattered light from the recess becomes weaker. Such a phenomenon was confirmed through our experiments.

Therefore, by observing the difference in intensity of the scattered light with the angle of incidence changed, i.e., by checking the degree of changes in the signals while the angle of incidence is changed, it is determined whether the object causing the scattering is a foreign matter or a recess.

On the basis of the knowledge as described above, in an aspect of the invention, light beams of two different wavelengths are focused on the same point in different angles of incidence, scattered light from the focused point are photoelectrically converted into signals for each of the two different wavelengths, and a foreign matter or flaw on the surface of the wafer and a recess in the form of a spot existing on the wafer surface are discriminated by utilizing the difference in strength of the signals.

For example, in one aspect of the invention, the surface inspection apparatus comprises two light sources emitting different wavelengths, an optical system configured, in focusing the light beams from the two light sources, such that the light beams of the two wavelengths are focused on the same point on the wafer surface in different angles of incidence, scanning means for scanning the focused point over a predetermined range on the wafer surface, two photoelectric converters adapted to sense the two wavelengths separately, a signal detector for detecting signals from the two photoelectric converters, and a discriminating portion utilizing the outputs from the signal detector for discriminating between a foreign matter or flaw on the wafer surface and a recess in the form of a spot existing on the wafer surface.

DESCRIPTION OF THE PREFERRED EMBODIMENTS

Figure 1:
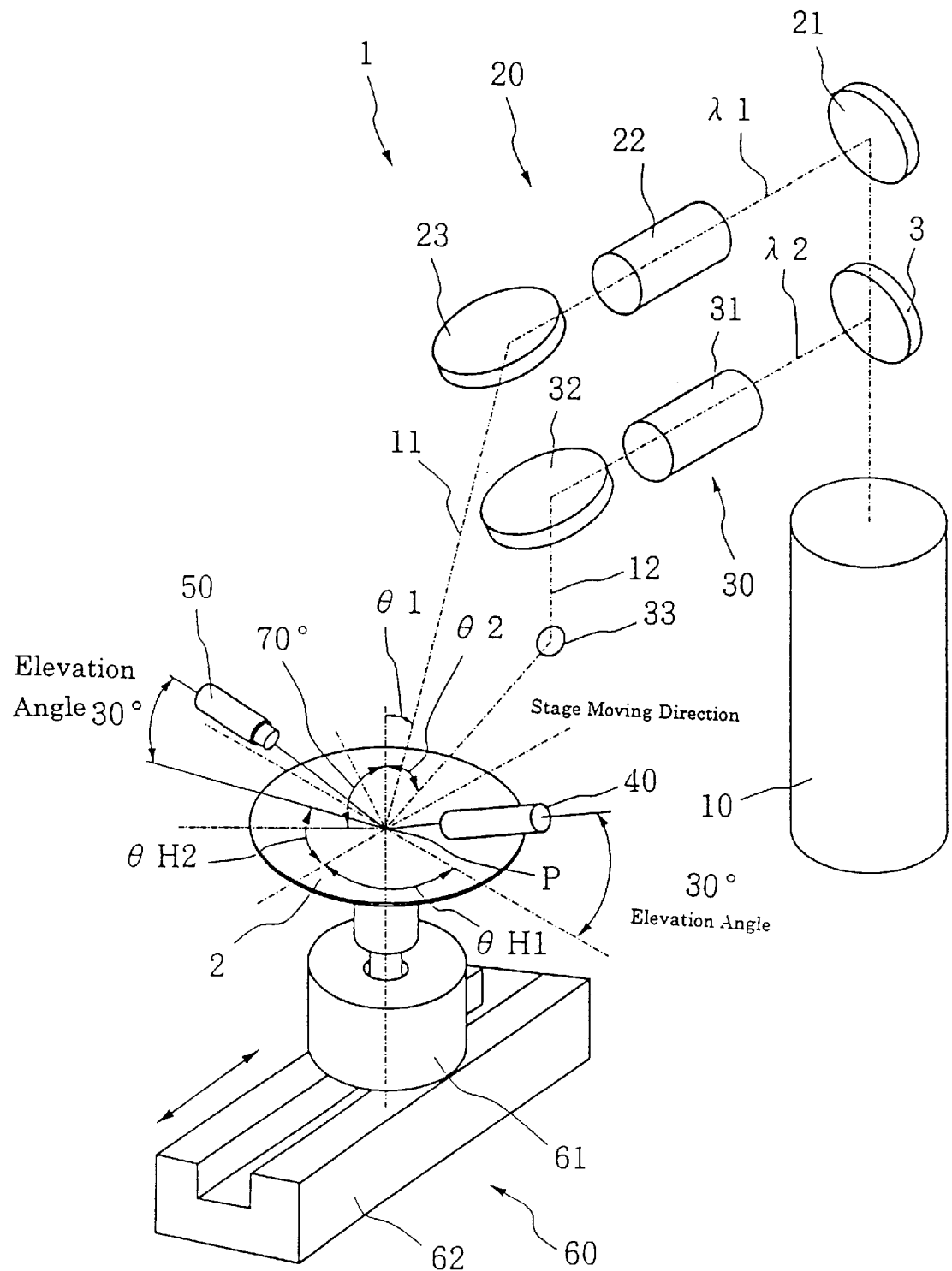
FIG. 1 is a general arrangement drawing of the main optical components of a surface inspection apparatus of the invention.

FIG. 1 is a schematic diagram showing arrangement of the main optical components of a surface inspection apparatus according to a preferred embodiment of the invention.

The surface inspection apparatus 1 comprises a light source portion 10 formed of a laser tube or the like emitting at least a light beam 11 of a first wavelength $\lambda 1$ and a light beam 12 of a second wavelength $\lambda 2$ different from the first wavelength, a first illuminating optical system 20 throwing the light beam 11 of the first wavelength $\lambda 1$ from the light source portion 10 onto a semiconductor wafer 2 as the inspected body in a first angle of irradiation 1, a second illuminating optical system 30 throwing the light beam 12 of the second wavelength $\lambda 2$ from the light source portion 10 onto the semiconductor wafer 2 at the same point of inspection P, as with the first illuminating optical system 10, in a second angle of irradiation $\theta 2$, a first photosensing optical system 40 for sensing in a first photosensing direction scattered light, from the point of inspection P on the surface of the semiconductor wafer 2, of the light beams 11, 12 thrown thereon by the first illuminating optical system 20 and the second illuminating optical system 30, a second photosensing optical system 50 for sensing in a second photosensing direction, different from the first photosensing direction, scattered light from the point of inspection P on the surface of the semiconductor wafer 2 of the light beams 11, 12 thrown thereon by the first illuminating optical system 10 or the second illuminating optical system 30, and a displacement portion 60 allowing the semiconductor wafer 2 as the inspected body to make linear and rotational movement relative to the light beam 11 thrown thereon by the first illuminating optical system 20. The elevation angle of the first photosensing optical system 40 is 30 degrees and the elevation angle of the second photosensing optical system 50 is 30 degrees.

Explaining the light source portion 10, any of the various types that emit light beams of a plurality of wavelengths can be used as the light source portion 10 emitting at least the light beam 11 of the first wavelength and the light beam 12 of the second wavelength different from the first wavelength. For example, such a one as a multi-line laser capable of emitting light beams of a plurality of wavelengths from one light source, or such a one in which light beams of a plurality of light sources emitting light beams of different wavelengths are combined into one beam by the use of a half mirror or the like, can be used.

If light beams of unnecessary wavelengths are generated when a multi-line laser is used, only the light beams of necessary wavelengths can be obtained by passing the emitted light beams through a bandpass filter which allows the first wavelength and the second wavelength to pass therethrough.

Figure 11:
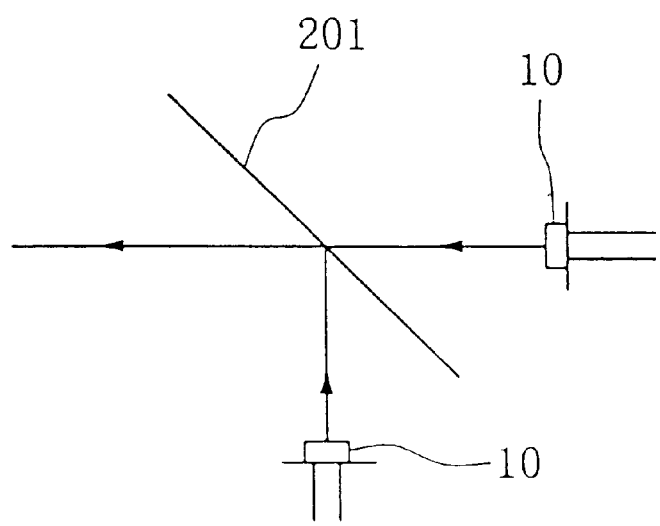
FIG. 11 is an explanatory drawing of an example of the manner to form one beam by combining a plurality of light beams with the use of a half mirror.

When a plurality of light sources emitting light beams of different wavelengths are used, the plurality of light beams are combined with a half mirror or the like into one beam. An example of the same is shown in FIG. 11. Light beams are emitted from the two light sources 10 and a combined beam is formed by combining the beams with the half mirror 201 inserted halfway through their courses. For example, a helium-cadmium laser is used and wavelengths of 441.6 nm and 325 nm are selected.

When an argon ion laser is used for the light source portion 10 in the example shown in FIG. 1, wavelengths of 488 nm and 514.5 nm can be selected. The light beams emitted from the light source portion 10 are separated into the light beam 11 of the first wavelength $\lambda 1$ and the light beam 12 of the second wavelength $\lambda 2$ by a dichroic mirror 3 which passes the light beam 11 of the first wavelength and reflects the light beam 12 of the second wavelength. The light beam 11 of the first wavelength is changed in its propagating direction by a first mirror 21 and thrown onto the irradiated point P on the surface of the inspected body 2 in an angle of irradiation $\theta 1$ through a group of first illuminating lenses 22 and a second mirror 23. The light beam 12 of the second wavelength is reflected by the dichroic mirror 3 and thrown onto the irradiated point P on the surface of the inspected body 2 in an angle of irradiation θ2 through a group of second illuminating lenses 31, a third mirror 32, and a fourth mirror 33.

When there is an object to be inspected such as a foreign matter present at the irradiated point P and the illuminating beam is cast thereon, scattered light is produced in accordance with predetermined directivity. The first angle of irradiation θ1 and the second angle of irradiation θ2 are set taking the direction of the normal line to the inspected body 2 as the reference. In the embodiment of FIG. 1, a specific angle is selected as the first angle of irradiation θ1 from the angles of incidence ranging from 0 degree to 40 degrees. As the second angle of irradiation θ2, a specific angle is selected from the angles ranging from 50 degrees to 85 degrees. Their horizontal directions may or may not be in agreement.

In the embodiment of FIG. 1, the relationship, the first angle of irradiation θ1<the second angle of irradiation θ2, holds true. The first wavelength λ1 and the second wavelength λ2 can be selected arbitrarily. However, since the detecting sensitivity becomes higher according as the angle of incidence is greater and there is such a tendency that the detecting sensitivity becomes higher according as the employed wavelength λ is shorter, if there exists the relationship that the second wavelength λ2 is shorter than the first wavelength λ1 (the first wavelength λ1>the second wavelength λ2), then the angles can be set so that the detecting sensitivity according to the first angle of irradiation θ1 and the detecting sensitivity according to the second angle of irradiation θ2 become equal.

Now, the first photosensing optical system 40 (sideward scattered light) and the second photosensing optical system 50 (forward scattered light) will be described.

To sense the above described scattered light, the first photosensing optical system 40 and the second photosensing optical system 50 are provided. The first photosensing optical system 40 senses, in the first photosensing direction, the scattered light from the inspected point P on the surface of the semiconductor wafer 2 of the light beams 11 and 12 thrown thereon by the first illuminating optical system 20 and the second illuminating optical system 30. The second photosensing optical system 50 senses, in the second photosensing direction different from the first photosensing direction, the scattered light from the inspected point P on the surface of the semiconductor wafer 2 of the light beam 11, 12 thrown thereon by the first illuminating optical system 20 or the second illuminating optical system 30.

A first photosensing horizontal angle θH1 (for example 90 degrees) of the first photosensing direction and a second photosensing horizontal angle θH2 (for example 50 degrees) of the second photosensing direction are determined taking, as the reference, the direction of the mirror reflection from the inspected body 2 of the illuminating light beams 11 and 12 thrown thereon by the first illuminating optical system 20 or the second illuminating optical system 30. In the embodiment of FIG. 1, the relationship, the first photosensing horizontal angle θH1>the second photosensing horizontal angle θH2, holds true.

The elevation angle of the first and the second photosensing directions is set for example at 30 degrees.

Figure 2:
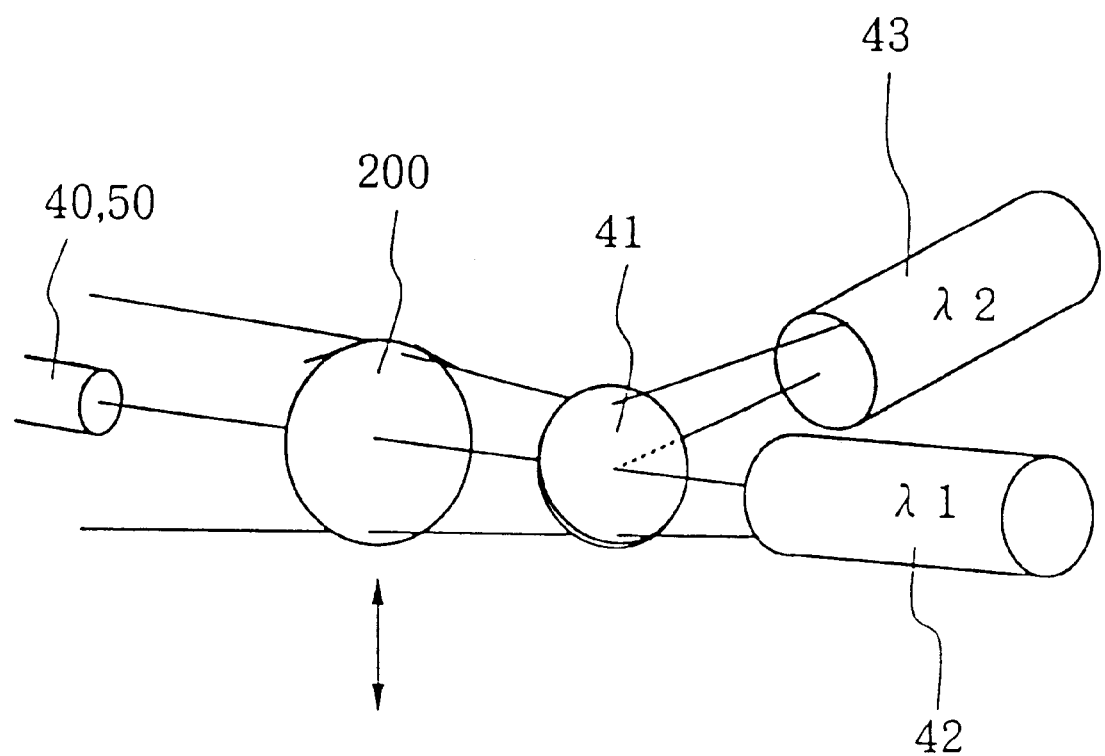
FIG. 2 is a detailed drawing of a photosensing optical system.

As shown in FIG. 2, the light beams sensed by the first photosensing optical system 40 are passed through an ND filter 200 disposed for movement in the directions of the arrowheads so as to be placed into and replaced from the photosensing optical path and then separated by a second dichroic mirror 41 into a light beam of the first wavelength λ1 and a light beam of the second wavelength λ2. A first photo detector 42 senses the scattered light of the first wavelength λ1 sensed by the first photosensing optical system 40 and converts the same into the first sensed-light signal. The second photo detector 43 senses the scattered light of the second wavelength λ2 sensed by the first photosensing optical system 40 and converts the same into the second sensed-light signal.

Also with the second photosensing optical system 50, configured similarly to that shown in FIG. 2, the sensed beams are passed through an ND filter disposed for movement in the directions of the arrowheads and then separated by a dichroic mirror 41 into a light beam of the first wavelength λ1 and a light beam of the second wavelength λ2. A third photo detector 43 senses the scattered light of the light beam of the first wavelength λ1 sensed by the second photosensing optical system 50 and converts the same into the third sensed-light signal. A fourth photo detector 44 senses the scattered light of the light beam of the second wavelength λ2 sensed by the second photosensing optical system 50 and converts the same into the fourth sensed-light signal.

As the first to the fourth photo detectors 41–44, use of photosensing elements of high sensitivity such as photomultipliers is preferred.

Now, the displacement portion 60 will be described. The displacement portion 60 is formed of a rotational displacement portion 61 for rotationally scanning the inspected body 2 and a linear displacement portion 62 for linearly scanning the inspected body 2. By adapting such that a fixed proportion of the width of the light beam is displaced linearly for each rotation of the rotational displacement portion 61, it is made possible to have the inspected body 2 spirally scanned all over the surface by the beams emitted from the first and the second illuminating optical systems 20 and 30.

The invention is not limited to the scanning method as described above. Instead of the described rotational displacement, the illuminating beams may be adapted to make linear scanning by means of a polygon mirror or the like.

In the embodiment of FIG. 1, the rotational displacement portion 61 is formed of a rotary motor for rotating the rotary table and the linear displacement portion 62 is formed of a slide shifting portion for linearly moving the rotary motor. The slide shifting portion by its shifting motion causes the irradiated position by the illuminating beams 11 and 12 from the illuminating optical systems 20 and 30 to pass across the inspected body 2 in the diametrical direction through the center.

Figure 3:
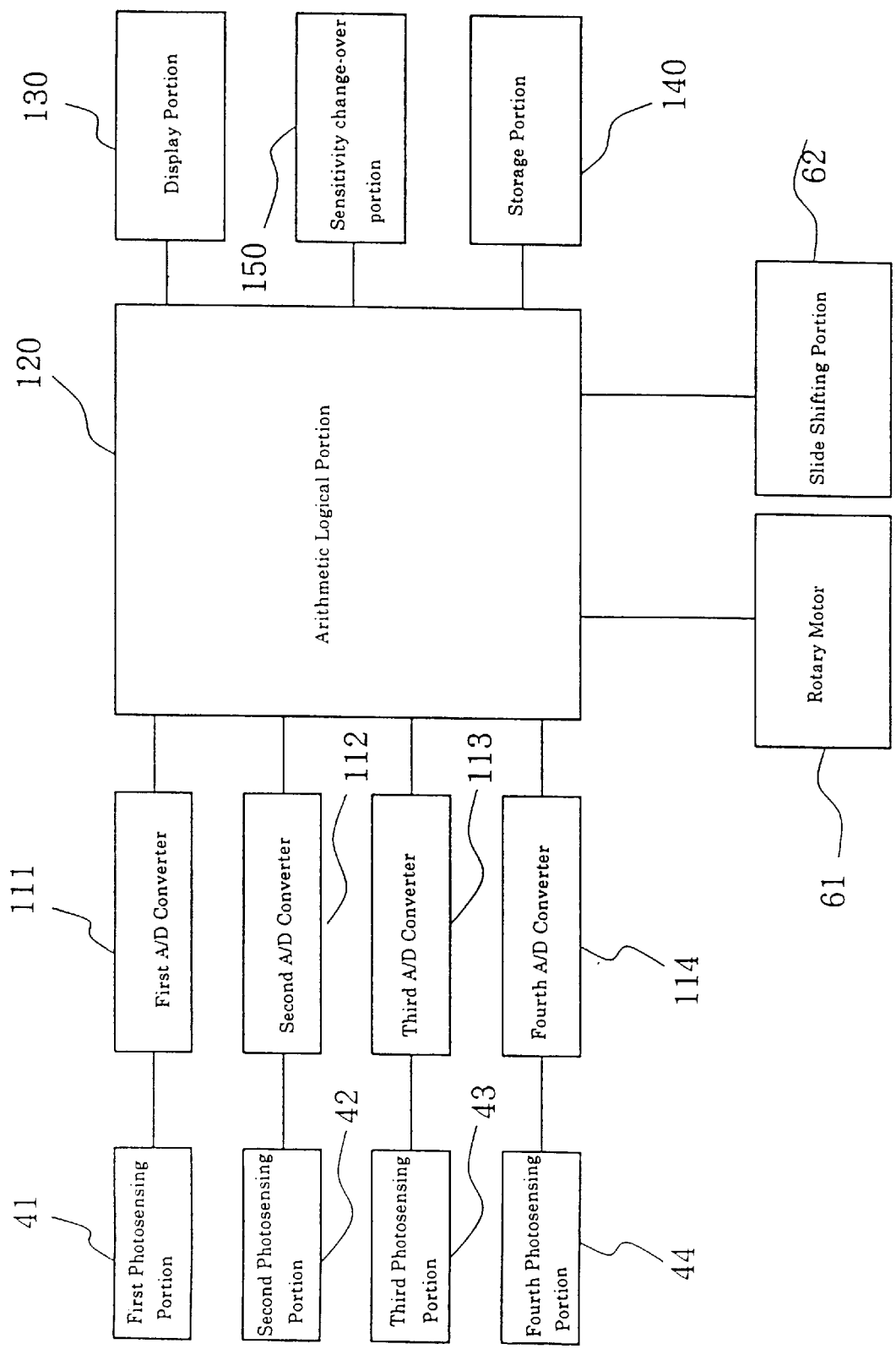
FIG. 3 is a block diagram showing an outline of the surface inspection apparatus of the invention.

FIG. 3 is a block diagram of the surface inspection apparatus according to the invention.

The first to fourth sensed-light signals sensed by the first to fourth photo detectors 41, 42, 43, and 44 are converted into digital signals by first to fourth A/D converters 111, 112, 113 and 114, respectively, and then sent to a control and arithmetic logical portion 120 serving as a signal processing portion and, therein, subjected to predetermined signal processing. The control and arithmetic logical portion 120 performs predetermined signal processing which is to be described later and displays the results of detection on a display portion 130 when necessary, stores the results in a storage portion 140, and reads out the stored contents.

The control and arithmetic logical portion 120 further controls the rotary motor of the rotational displacement portion 61 and the slide shifting portion of the linear displacement portion 62, and controls a sensitivity changeover portion 150 for the first to fourth photo detectors 41, 42, 43, and 44 according to the kinds of the inspected body 2.

The sensitivity change-over portion 150 performs the sensitivity change-over by moving the ND filter 200 in the directions of the arrowheads in FIG. 2, i.e., it decreases the sensitivity by applying the ND filter 200 to the light receiving windows of the first to fourth photo detectors 41, 42, 43, and 44 or increases the sensitivity by removing the ND filter 200 from the light receiving windows.

When the first to the fourth photo detectors 41, 42, 43, and 44 are formed of photomultipliers, the sensitivity may also be changed by adjusting the voltage applied to the photomultipliers.

Figure 4:
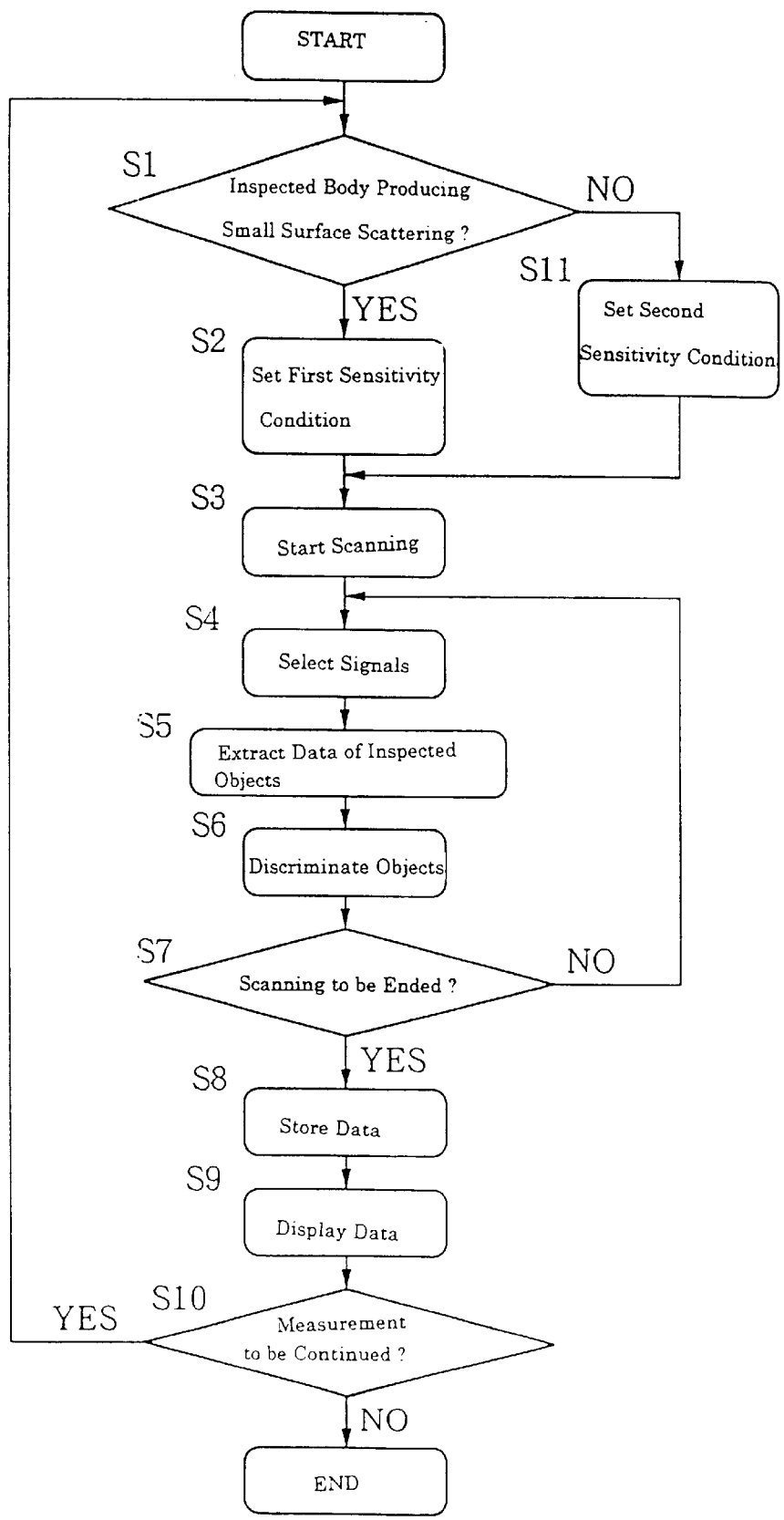
FIG. 4 is an outline flowchart of the inspection performed in the surface inspection apparatus to which the invention is applied.

FIG. 4 shows the inspecting procedure in outline.

When the inspection is started, the kind of the inspected body 2 is determined in step S1, i.e., it is determined whether it produces small surface scattering (for example, a bare wafer or a wafer coated with an SiO2 film) or it produces great surface scattering (for example, a wafer coated with a metallic film). When the inspected body 2 is that producing small surface scattering, the processing advances to step S2 and the sensitivity of the first to the fourth photo detectors 41–44 is set to that which is suited to the inspected body producing small surface scattering. Namely, when the inspected body is that producing small surface scattering, the sensitivity of the first photo detector 41 and the third photo detector 43 is changed over to the high sensitivity and the sensitivity of the second photo detector 42 and the fourth photo detector 44 is changed over to the low sensitivity (this condition is called the first inspecting condition), and then the processing advances to step S3.

In step S3, the displacement portion 60 makes rotational displacement and linear displacement so that a spiral scan is performed, while both the first light beam 11 of the first wavelength λ1 and the second light beam 12 of the second wavelength λ2 are thrown from the first illuminating optical system 20 and the second illuminating optical system 30, and the processing advances to step S4.

In step S4, the control and arithmetic logical portion 120 receives the first to fourth sensed-light signals from the first to fourth photo detectors 41–44 and the sensed-light signals to be subjected to signal processing are selected therefrom. Then, the processing advances to step S5.

In step S5, the control and arithmetic logical portion 120 applies predetermined signal processing to the selected sensed-light signals, extracts therefrom inspected objects (for example, projecting foreign matters, recessed crystalline defects, and the like), and obtains such data as the starting coordinates, the ending coordinates, and the peak coordinates of the inspected objects. Then, the processing advances to step S6.

In step S6, kinds of the inspected objects (for example, projecting foreign matters and recessed crystalline defects) are determined in accordance with the extracted data with high-angle irradiation and the extracted data with low-angle irradiation and, then, the processing advances to step S7.

In step S7, it is decided whether or not the scanning should be ended. When the scanning is not to be ended, the processing returns to step S4 and the scanning process is repeated until it is completed. When the scanning is completed, the processing advances to step S8.

In step S8, the inspection data of the inspected objects are stored in the storage portion 140 and the processing advances to step S9.

In step S9, the later described inspection data of the inspected objects are displayed on the display portion 130 in predetermined formats and the processing advances to step S10.

In step S10, it is determined whether or not the measurement is completed. If it is not completed, the processing returns to step S1 and the measurement is made anew. Otherwise, the inspection is ended at this point.

When it is determined in step S1 that the inspected body 2 is that producing great surface scattering (for example, a wafer coated with a metallic film), the processing advances to step S11, where the sensitivity of the first to fourth photo detectors 41–44 is set at that which is suitable for the inspected body producing great surface scanning. Namely, when the inspected body is that producing great surface scattering, the sensitivity of the first photo detector 41 and the third photo detector 43 is changed over to the low sensitivity and the sensitivity of the second photo detector 42 and the fourth photo detector 44 is changed over to the high sensitivity. This condition is called the second inspecting condition. Then, the processing advances to step S3 and, thereafter, inspecting processes as described above are performed.

The selection of the sensed-light signals is carried out as follows.

The signal selecting process performed in step S4 of FIG. 4 will be described below.

When the inspected body 2 is such that produces small surface scattering (such as a bare wafer and a wafer coated with an SiO2 film), the sensitivity of the first to fourth photo detectors 41–44 is set at that suitable for the inspected body producing small surface scattering. Namely, when the inspected body is that which produces small surface scattering, the sensitivity of the first photo detector 41 and the third photo detector 43 is changed over to the high sensitivity and the sensitivity of the second photo detector 42 and the fourth photo detector 44 is changed over to the low sensitivity. This condition is called the first inspecting condition. The inspection is performed under this condition.

At this time, scattered light of the first wavelength λ1 of a light beam thrown at a high angle is sensed by the first photo detector 41 set at the high sensitivity and the second photo detector 42 set at the low sensitivity and, thereby, the first sensed-light signal and the second sensed-light signal are formed.

Scattered light of the second wavelength λ2 of a light beam thrown at a low angle is sensed by the third photo detector 43 set at the high sensitivity and the fourth photo detector 44 set at the low sensitivity and, thereby, the third sensed-light signal and the fourth sensed-light signal are formed. Examples of the sensed light signals at this time are shown in FIGS. 5 (1), (2), (3), and (4).

Figure 5:
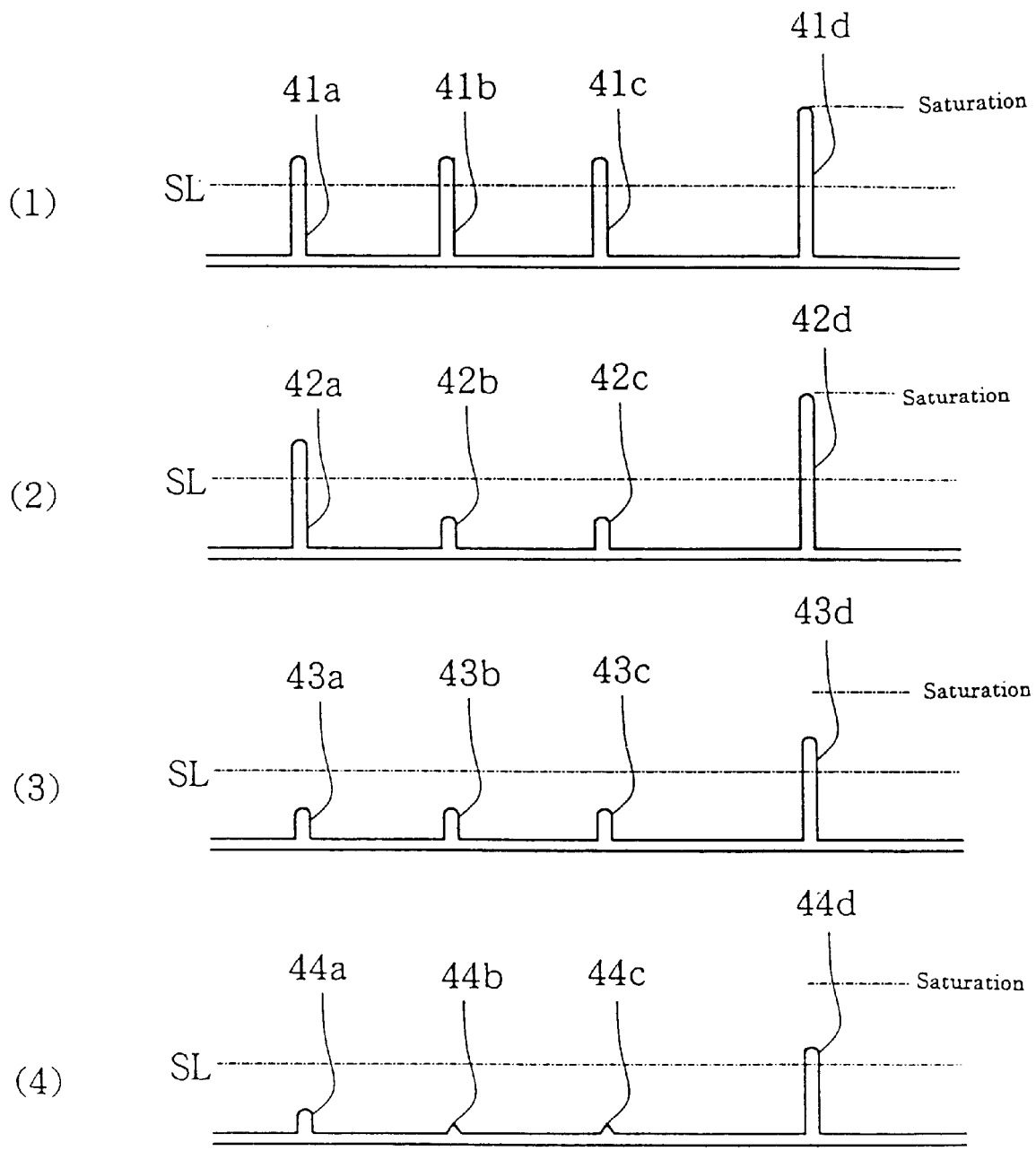
FIG. 5 is a drawing showing an example of a first sensed-light signal to a fourth sensed-light signal.

As shown in FIG. 5, the sensed-light signals to be subjected to the signal processing for extracting the inspected objects are selected according to the intensity of the scattered light from the inspected object. As an example, when any of the first sensed-light signal segments 41*a*–41*d* as the output of the first photo detector 41 set at the high sensitivity is not saturated, the first sensed-light signal is selected as the signal for signal processing of scattered light of the first wavelength λ1. When at least one of the first sensed-light signal segments 41*a*–41*d* is saturated, the second sensed-light signal 42*a*–42*d* as the output of the second photo detector 42 set at the low sensitivity is selected as the signal for signal processing of scattered light of the first wavelength λ1. Thus, a scattering characteristic with high-angle irradiation is obtained.

On the other hand, in obtaining a scattering characteristic with low-angle irradiation, the third sensed-light signal 43*a*–43*d* is selected as the signal for signal processing of scattered light of the second wavelength λ2 when all the segments 43a–43d of the third sensed-light signal as the output of the third photo detector 43 set at the high sensitivity are not saturated, whereas, if any of the third sensed-light signal segments 43a–43d is saturated, the fourth sensed-light signal 44a–44d as the output of the fourth photo detector 44 set at the low sensitivity is selected as the signal for signal processing of scattered light of the second wavelength λ2.

Further, the method of processing the signals extracted from the data of inspected objects will be described in concrete terms.

The processing of the data of the inspected objects is performed in step S5 shown in FIG. 4. Describing the process for extracting the data of the inspected objects, there are various systems to express the inspected objects. As an example, that determining the inspected object by its starting coordinates, ending coordinates, and peak coordinates will be described.

Figure 6:
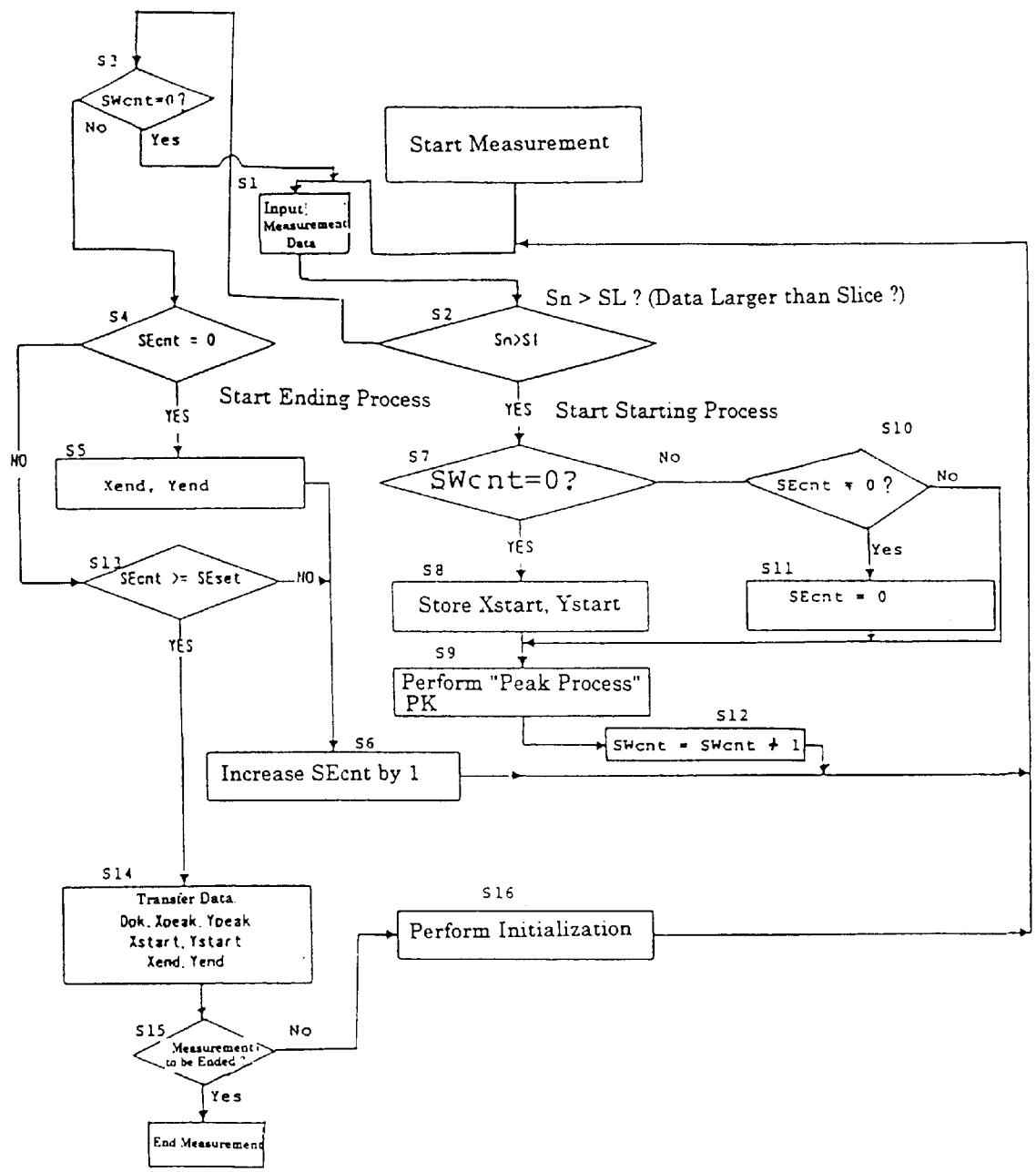
FIG. 6 is a flowchart showing an example of the signal processing for obtaining objects of inspection in the surface inspection apparatus of the invention.

FIG. 6 is an example of the flowchart of such a method according to the invention.

In FIG. 6, first, when the measurement is started, the measured data is input in step 1 and the processing advances to step 2.

In step 2, it is determined whether or not the obtained measurement data Sn is greater than the slice level SL and, when it is smaller than that, the processing advances to step 3, while, when it is greater than that, the processing advances to step 7.

In step 3, it is determined whether or not the count of width SWcnt, which indicates the width of a foreign matter, is 0, i.e., whether or not the measurement data Sn has already exceeded the slice level SL. In other words, it is determined whether or not the data of a foreign matter was measured immediately before. Here "immediately before" means within the count of the predetermined value SEset, which is determined in step 13.

When the count of the SWcnt is 0, i.e., when there was no data of a foreign matter immediately before, the processing returns to step 1 and, therein, processing of the next measured data is started. When the count of the SWcnt is not 0, i.e., when there was present data of a foreign matter immediately before, the processing advances to step 4 and, therein, processing to take SEcnt count (count of non-signal period), i.e., to count the period during which the obtained measurement data Sn is smaller than the slice level SL, is performed.

When SEcnt=0 in step 4, it is determined whether or not an end signal count is 0, and when SEcnt=0, the processing advances to step 5. Otherwise, it advances to step 12.

In step 5, namely where the obtained measurement data Sn has lowered from the state of its being above the slice level SL to the state of its being below the slice level SL, the X and Y coordinates at this time are stored as Xend and Yend and the processing advances to step 6. In step 6, the SEcnt value is increased by 1 and the processing returns to step 1 and, therein, processing of the next measured data is started.

When it is determined in step 2 that the obtained measurement data Sn is greater than the slice level SL, the processing advances to step 7. In step 7, it is determined whether or not the count of SWcnt is 0, i.e., it is determined whether the measurement data Sn has ever exceeded the slice level SL. When it has exceeded it for the first time, the processing advances to step 8. If it is not for the first time, the processing advances to step 10.

In step 8, the coordinate values at this point are stored as the starting coordinates (the coordinates values of the starting point) Xstart and Ystart of the foreign matter and the processing advances to step 9.

On the other hand, when it is determined in step 7 that the count value SWcnt from the start of a foreign matter is not 0, i.e., that it is not for the first time for the measurement data Sn to have exceeded the slice level SL, the processing advances to step 10 and, therein, it is determined whether the count value of the non-signal period count SEcnt is not 0. When the non-signal period count SEcnt is not 0, the count value of the count SEcnt is reset to 0 in step 11 and the processing advances to step 9. When the non-signal period count SEcnt is 0, the processing directly advances to step 9.

In step 9, peak processing is made to determine whether or not the obtained measurement data at this time is greater than that obtained previously and store the greater of them as the peak data and the processing advances to step 12.

In step 12, 1 is added to the count value SWcnt from the point of the starting coordinates of the foreign matter (the starting point, corresponding to the front edge of the foreign matter) and the processing returns to step 1.

When SEcnt≠ 0, i.e., when the count value of the non-signal period count SEcnt is not equal to 0, the processing advances to step 13. It is determined, therein, whether or not the non-signal period count SEcnt is greater than a preset count value SEset. When the non-signal period count SEcnt is smaller than the preset count value SEset, the processing advances to step 6 for processing the next measured data.

On the other hand, when the non-signal period count SEcnt is greater than the preset count value SEset, the processing advances to step 14.

In step 14, data of the coordinate values Xstart, Ystart of the starting point of the foreign matter stored in step 8, the coordinate values Xend, Yend stored in step 5, and the peak value stored in the memory are transferred to be stored into memory as the coordinate values of the starting point, the coordinate values of the ending point, and the peak value of the foreign matter under the current inspection and the processing advances to step 15.

In step 15, it is determined whether the measurement has been completed. When it is determined that the measurement has been completed, the measurement is ended at this point. If not, the processing advances to step 16.

In step 16, initialization is made, i.e., the coordinate values Xstart, Ystart of the starting point of the foreign matter, the ending coordinate values Xend, Yend, the peak value P, the non-signal period count SEcnt, and the count value SWcnt from the start of the foreign matter are reset to 0 and the processing returns to step 1.

Figure 7:
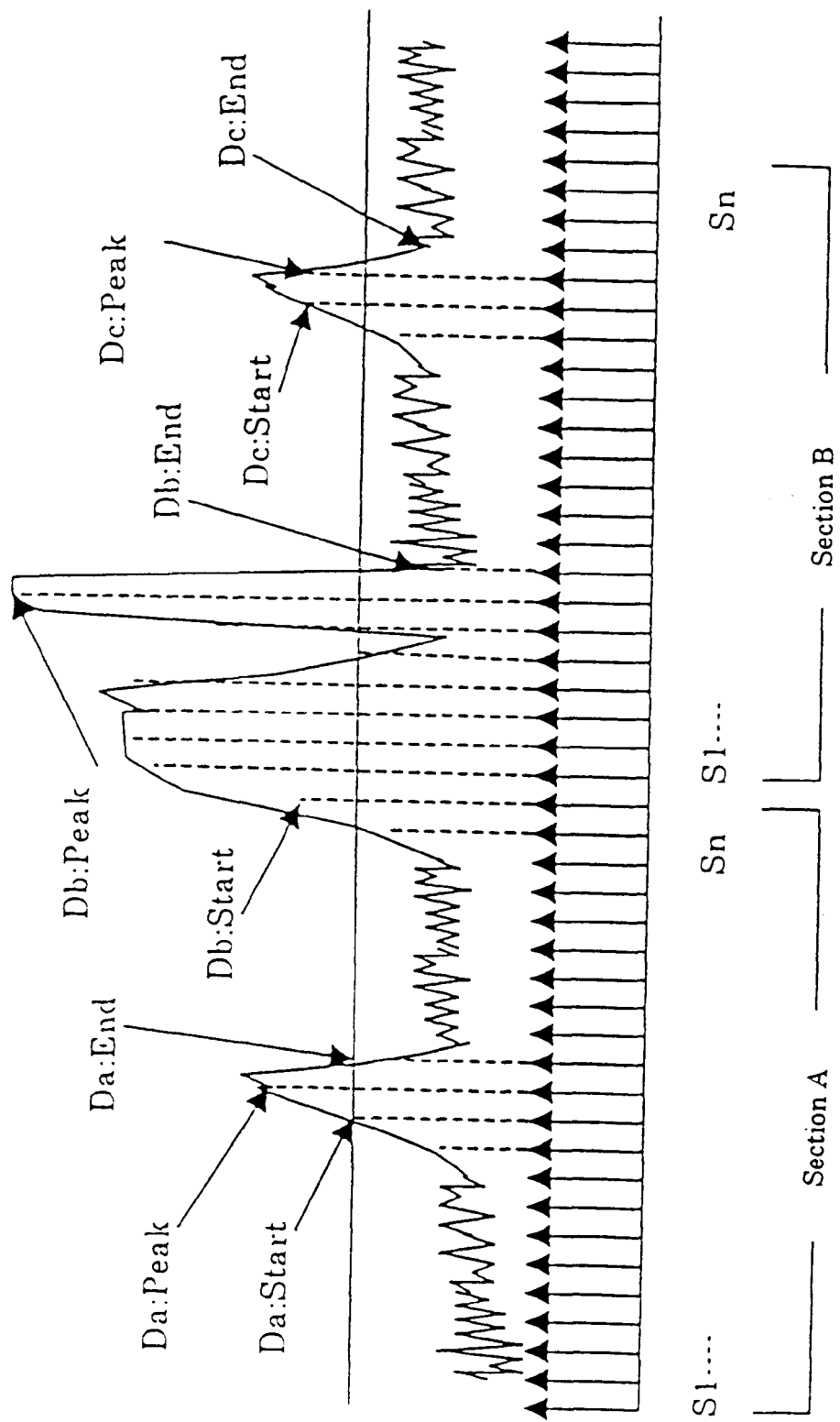
FIG. 7 is a drawing showing an example of the sensed-light signal.

FIG. 7 shows a method of processing peak values and the like.

When a scattered light beam from a foreign matter has exceeded the threshold signal (indicated by the horizontal solid line in FIG. 7) while the detecting light beam is scanned in a predetermined direction, the point is stored as a starting point (Start) and, when thereafter the scattered light beam has fallen below the threshold signal, the point is stored as an ending point (End) and, then, the point between the starting point and the ending point where the foreign matter-scattered signal is at a maximum is stored as a peak (Peak). The foreign matter on the surface of the inspected body is particularized on the basis of the positional information, as the positional data of the foreign matter-scattered signal, composed of the starting point (Start), the peak (Peak), and the ending point (End).

In FIG. 7, since the foreign matters are specified by Da, Db, and Dc, the number of the foreign matters is known as 3. In this case, the data of the section A and the section B are not related to the number of the foreign matters but the number of the foreign matters is counted as 3.

Now, detection in Z direction will be described.

The height of an inspected body 2 can be found from the sensed position obtained through sensing the mirror reflection light of the illuminating light beam. According to the need, it is also possible to compensate for the coordinate of the position of the inspected body in Y direction (the direction of the linear traveling of the inspected body 2). For example, when the height of the inspected body has made a displacement of dZ referenced from the reference plane while the surface of a wafer 2 is inspected, an arithmetic and synchronizing circuit portion provides, on the basis of the output signal from the photo detector, compensation to the coordinates Ym . . . in the radial direction, which are obtained by the peak detecting circuit portion, of an amount of dY, given by $dY=dZ/\tan \theta$, where $\theta$ is the angle formed between the light beam cast on the reference plane and the reference plane. For example, the peak position, after the compensation, is given by Ym data—dY. While a discrepancy in the coordinate value occurs only in the radial direction in the case of the spiral scanning, such compensation can be provided in the case of other scanning systems to the coordinate values in the directions in which discrepancies are produced due to a change in the height.

Now, discrimination between the inspected objects will be described.

Description will be made in more concrete terms about discrimination between types of the inspected objects performed in step 7 of FIG. 4.

Here, the kind of an inspected object is identified on the basis of extracted data from the result with high-angle irradiation and extracted data from the result with low-angle irradiation.

When an inspected body 2 producing small surface scattering is inspected, various kinds of the first to fourth sensed-light signals as shown in FIGS. 5(1), 5(2), 5(3), and 5(4) are obtained. These sensed-light signals include signals of small foreign matters on the surface corresponding to projections on the surface, signals of crystalline defects corresponding to recesses on the surface, and signals of large foreign matters corresponding to projections on the surface.

For example, the first sensed-light signal 41a–41d shown in FIG. 5(1) is that output from the first photo detector 41 set at the high sensitivity and sensing, in the first direction, the scattered light of a light beam of the wavelength λ1 thrown in the high angle of irradiation. The first sensed-light signal segments 41a–41d include a signal segment of a foreign matter corresponding to a projection on the surface and a signal segment of a crystalline defect corresponding to a recess on the surface, as signal segments exceeding the slice level SL. However, the signal segment 41d on the rightmost side is saturated.

The second sensed-light signal 42a–42d shown in FIG. 5(2) is that output from the second photo detector 42 set at the high sensitivity and sensing in the first direction the scattered light of a light beam of the wavelength λ2 thrown in the low angle of irradiation. In the second sensed-light signal segments 42a–42d, there are present the signal segments 42a and 42d of foreign matters corresponding to projections on the surface as only signals exceeding the slice level SL while there are present the signal segments 42b and 42c of crystalline defects corresponding to recesses on the surface as signals lower in level than the slice level SL. However, the signal segment 42d on the rightmost side is saturated.

The third sensed-light signal 43a–43d shown in FIG. 5(3) is that output from the third photo detector 43 set at the low sensitivity and sensing in the second direction the scattered light of a light beam of the wavelength λ1 thrown in the high angle of irradiation. The third sensed-light signal segments 43a–43d shown in FIG. 5(3) appear as those obtained by having all of the first sensed-light signal segments 41a–41d lowered in level.

The fourth sensed-light signal 44a–d4d shown in FIG. 5(4) is that output from the fourth photo detector 44 set at the low sensitivity and sensing in the second direction the scattered light of a light beam of the wavelength λ2 thrown in the low angle of irradiation. The fourth sensed-light signal segments 44a–44d shown in FIG. 5(4) appear as those obtained by having all of the third sensed-light signal segments 43a–43d lowered in level.

Accordingly, an object appearing in both of the sensed-light signal obtained when radiation is made in the high angle of irradiation (the first sensed-light signal or the third sensed-light signal) and the sensed-light signal obtained when radiation is made in the low angle of irradiation (the second sensed-light signal or the fourth sensed-light signal) can be identified as a projection on the surface (i.e., a foreign matter). On the other hand, an object appearing in the sensed-light signal obtained when radiation is made in the high angle of irradiation (the first sensed-light signal or the third sensed-light signal) and not appearing in the sensed-light signal obtained when radiation is made in the low angle of irradiation (the second sensed-light signal or the fourth sensed-light signal) can be identified as a recess (i.e., a recess due to a crystalline defect or the like).

On the display portion 130, the inspected objects are displayed separately for each type thereof or all types of the inspected objects put together are displayed such that the types of the inspected objects can be discriminated from each other. Further, when the data obtained by measurements of the same inspected body in the past are available, such history as increase, decrease, and the like of the inspected objects (foreign matters and the like) is displayed in the form understandable by a graph or the like.

Figure 8A:
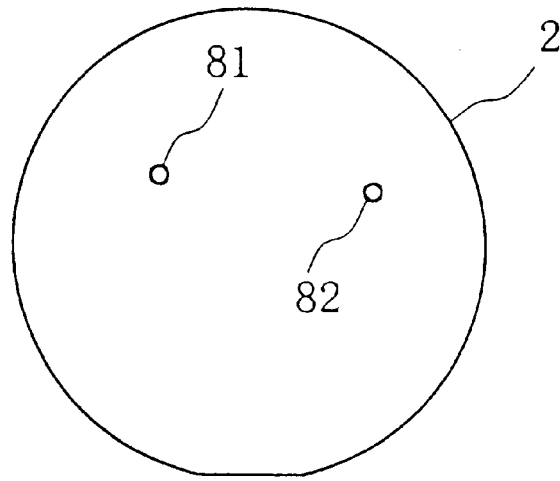
FIGS. 8a–8c are drawings showing an example of displays of results of inspection made in the surface inspection apparatus of the invention, in which displays are grouped by the kind of the inspected objects or arranged for all of the kinds in a composite manner.
Figure 8B:
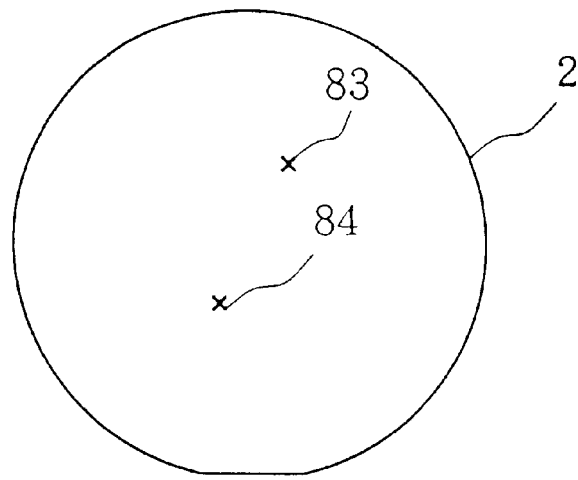
Figure 8C:
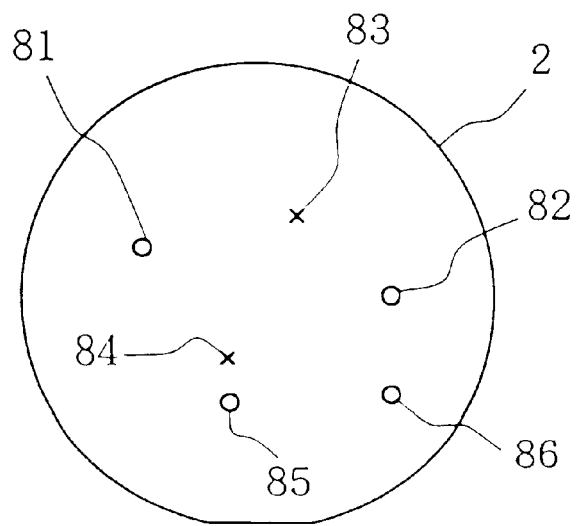

Examples of displaying such results of inspection are shown in FIGS. 8a–8c. In FIG. 8a, only crystalline defects detected in a contour of an inspected body 2 are displayed associated with the detected positions by ○ 81, 82. In FIG. 8b, only foreign matters detected in the contour of the inspected body 2 are displayed associated with the detected positions by X 83, 84. In FIG. 8c, both the crystalline defects and the foreign matters detected in the contour of the inspected body 2 are displayed associated with the detected positions with symbols (such as ○ and X) attached thereto so that they can be distinguished from each other.

Further, it is preferable to display the values of the peaks described with reference to FIG. 7 in different colors.

FIGS. 9a–9c and FIG. 10 are drawings showing examples of displays of history, such as increase or decrease of inspected objects, made up when data of measurement of the same inspected body in the past are available.

Figure 9A:
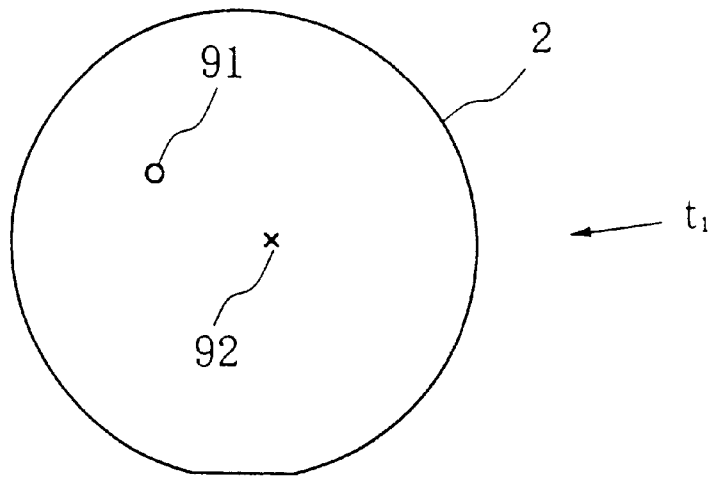
FIGS. 9a–9c are drawings showing another example of displays of results of inspection obtained by the surface inspection apparatus of the invention associated with results of measurement carried out in the past.
Figure 9B:
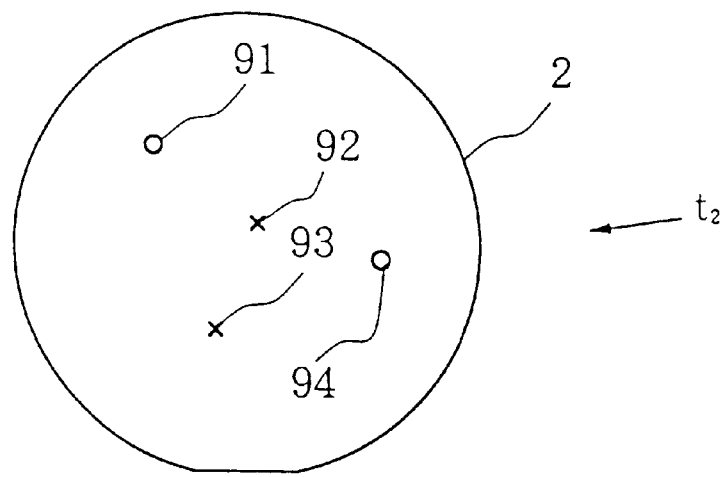
Figure 9C:
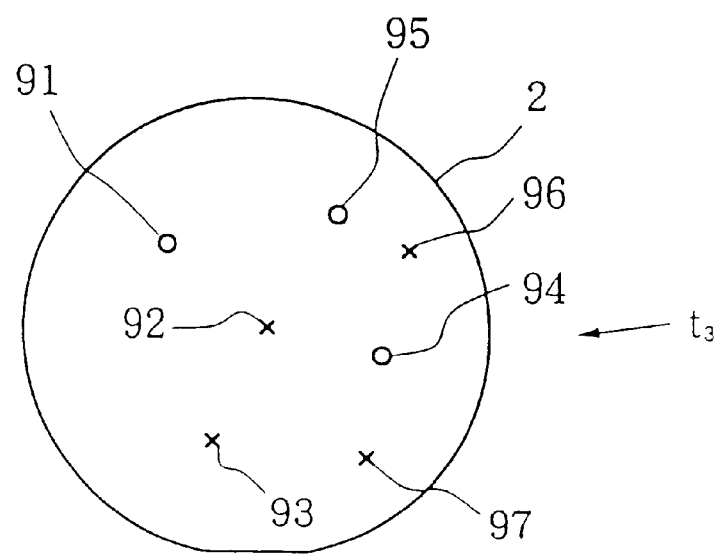

FIG. 9a shows inspected data obtained at the first time (t1), FIG. 9b shows inspected data obtained at the second time (t2), and FIG. 9c shows inspected data obtained at the third time (t3). Numerals 91, 94, and 95 with the symbol ○ denote inspected objects in a recessed form (crystalline defect or the like) and numerals 92, 93, 96, and 97 with the symbol X denote inspected objects in a projecting form (projecting matters such as particles). The numbers of the inspected objects progressively increased as seen from FIG. 9a to FIG. 9c.

Figure 10:
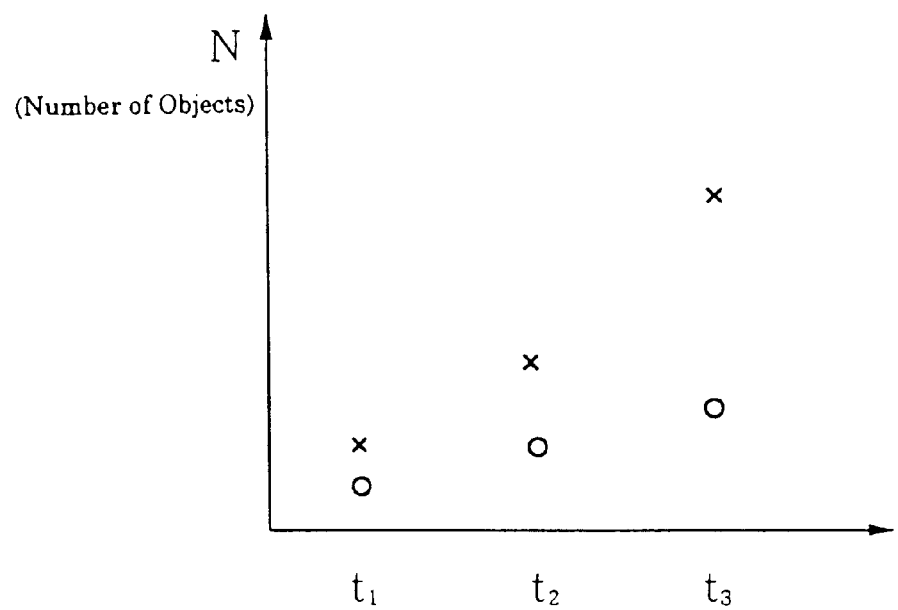
FIG. 10 is a drawing showing an example of a display of results of the inspection obtained by the surface inspection apparatus of the invention associated with results of inspection carried out in the past.

FIG. 10 is a graph showing the history of the inspected objects 91–97 from FIG. 9a to FIG. 9c, i.e., during the period of times (t1)–(t3).

FIG. 11 shows an example of the arrangement to combine a plurality of beams into one beam with a half mirror.

Figure 12:
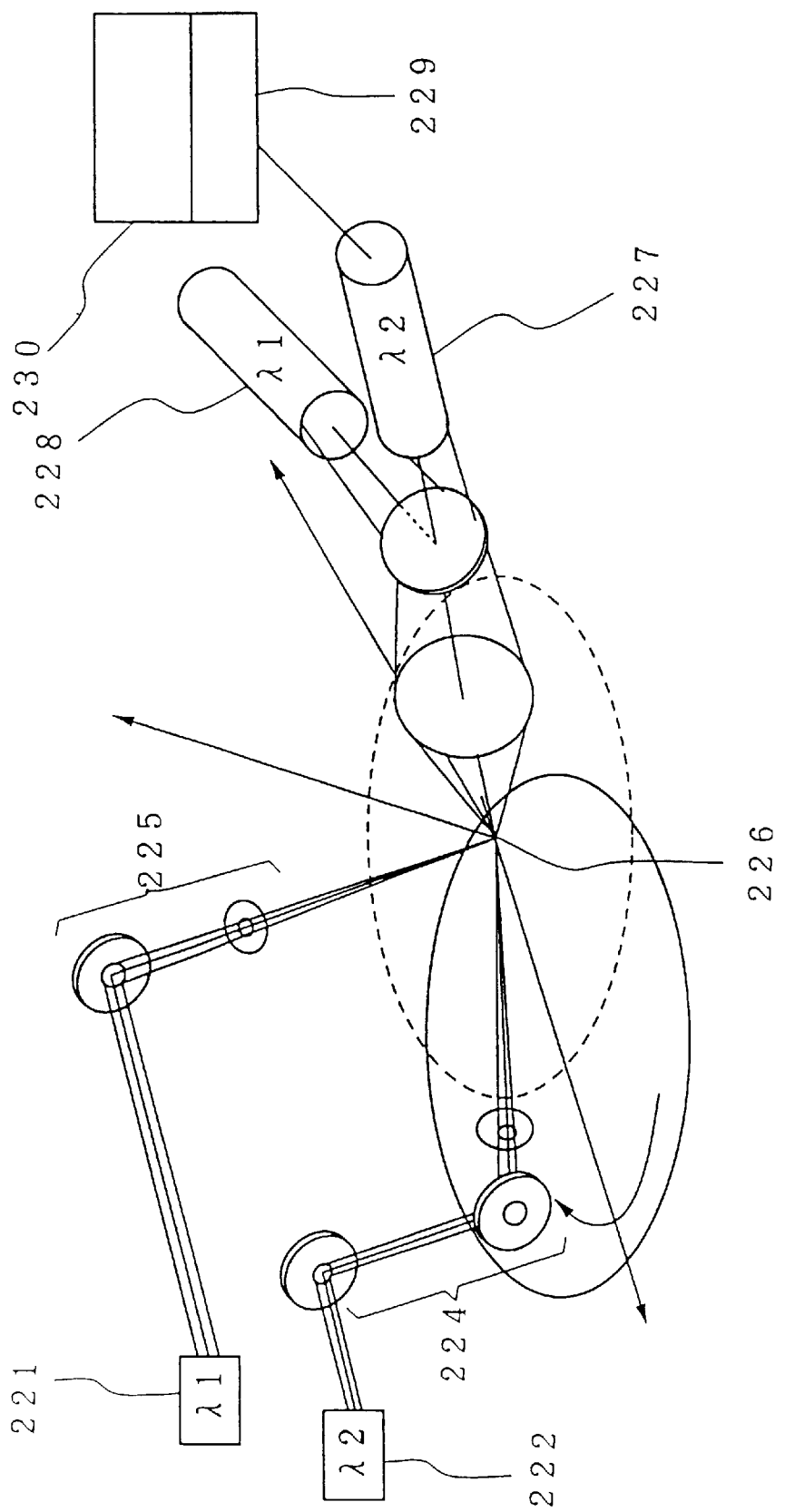
FIG. 12 is a general arrangement drawing of another preferred embodiment of the invention.

FIG. 12 shows another embodiment of the invention.

The wafer surface inspection apparatus shown in FIG. 12 comprises two light sources 221, 222 for different wavelengths, optical systems 224, 225 adapted to focus light beams from the two light sources 221, 222 on the surface of a wafer 223 such that the light beams of two wavelengths are focused on the same point on the surface of the, wafer 223 in different angles of incidence, scanning means (not shown) for allowing the focused point 226 to scan over a predetermined range (for example, the total range) of the surface of the wafer 223, two photoelectric converters 227, 228 each thereof being adapted, when sensing scattered light from the focused point 226, to sense each of the two wavelengths, a signal detector 229 for detecting signals from the two photoelectric converters 227, 228, and a discriminating portion 230 for discriminating foreign matters, scratch, and the like on the wafer surface from recesses in a spot form existing on the wafer surface making use of the output from the signal detector 229.

As the light sources 221 and 222, lasers are used. The light beams emitted from the light sources 221 and 222 are focused on the surface of the wafer 223 through separate optical systems 224 and 225. The light beams emitted from the light sources 221 and 222 are focused on the surface of the wafer 223 so as to measure objects at the same time and at the same point. Further, it is adapted such that two illuminating light beams of wavelengths relatively close to each other (for example, 488 nm and 514.5 nm) are used and the beams irradiate the wafer 223 in two different angles of incidence (for example, 20 degrees and 70 degrees). Further, the two photoelectric converters 227 and 228 sense scattered light of the two light beams of the different wavelengths relatively close to each other in the same orientation and angle with respect to the plane of incidence and output signals. The signal detector 229 detects the signals from the two photoelectric converters 227 and 228 and the discriminating portion 230, in turn, discriminates foreign matters, scratch, or the like on the wafer surface from recesses in a spot form existing on the wafer surface by making use of the output signal from the signal detector 229.

Figure 13:
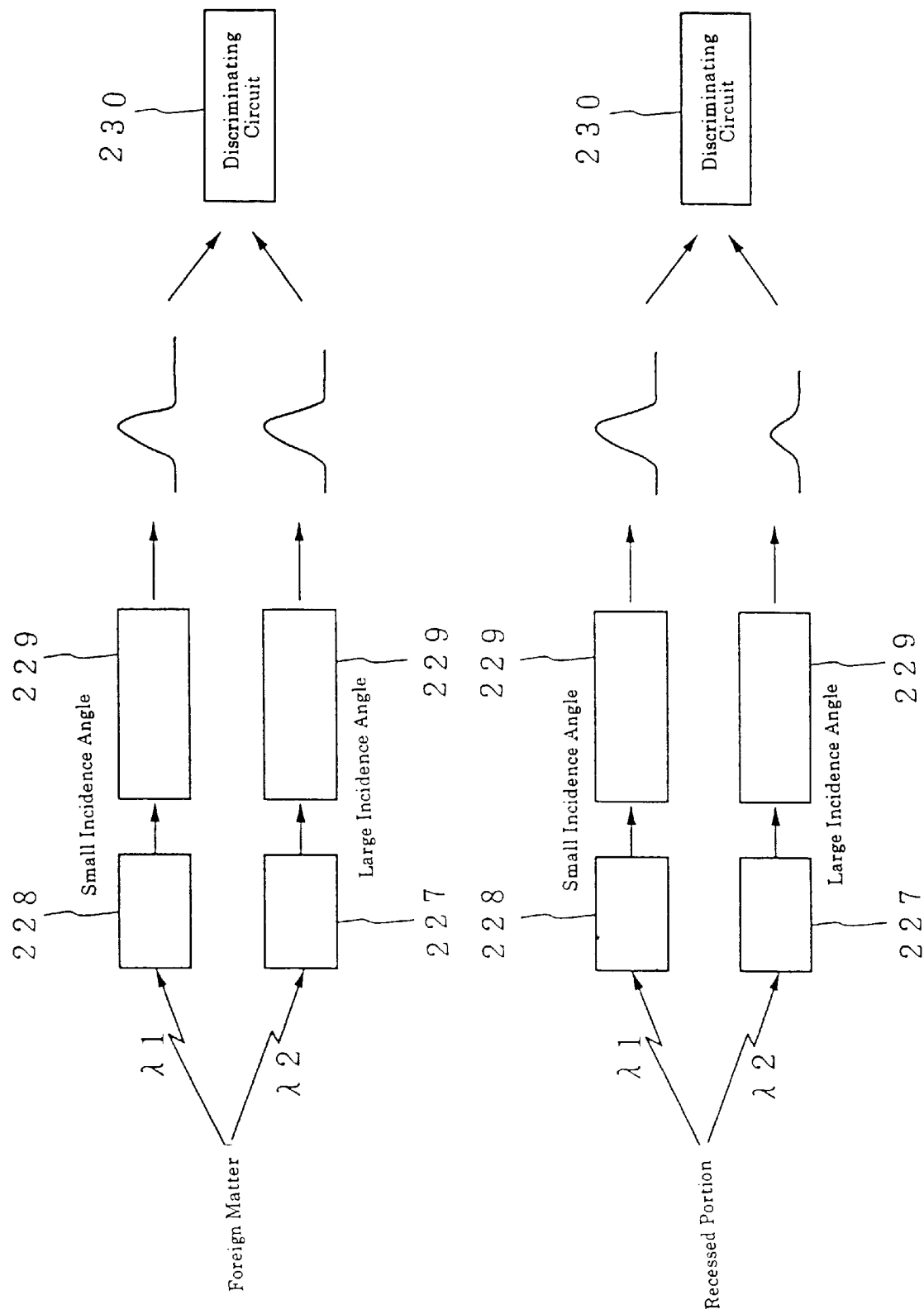
FIG. 13 is a schematic diagram showing examples used for discriminating between a foreign matter and a recess in the embodiment of FIG. 12.

FIG. 13 shows comparison between examples of signals output from a foreign matter and signals output from a recess, which produce scattered light on the same intensity level.

The discrimination between a recess in a spot form and a foreign matter on the wafer surface is made as follows. Namely, changes in intensity of the scattered light according to changes in the angle of incidence are detected while the orientation and angle of the two photoelectric converters 227 and 228 are fixed. Changes in intensity of scattered light from a foreign matter attached to the surface of the wafer are detected and, at the same time, changes in intensity of scattered light from a minute recessed portion on the surface of the wafer are detected. In comparison of both the changes with each other as shown in FIG. 13, both the signals become relatively large when the angle of incidence is small and, therefore, it is difficult to discriminate between them, but, when the angle of incidence is large, the signal of the foreign matter becomes relatively larger than the signal of the recess, and, therefore, discrimination between them can be achieved easily.

Thus, by comparing differences in intensity of the scattered light when the angle of incidence is changed, i.e., by comparing the changes in the signals when the angle of incidence is changed, it can be determined whether the scattering matter is a foreign matter or it is a recess.

The discriminating portion can be a discriminating circuit or a discriminating program.

Although there is the possibility that a recess in a spot form and a scratch in a recessed form become indistinguishable, the distinction can be made, because a scratch in general is relatively larger (longer) than a foreign matter or a recess in a spot form, by checking whether or not the signal is present in an isolated manner (whether or not the signal is present also on plural adjoining scanning lines).

Although, in the above described embodiment shown in FIG. 12 and FIG. 13, the different angles of incidence were set to be on the same plane of incidence, the angles of incidence may be on the different planes of incidence provided that photosensing is made in the same orientation and direction with respect to the plane of incidence.

Although, in the above described embodiment shown in FIG. 12 and FIG. 13, the scanning system called the spiral scanning system employing a mechanism for rotating and linearly shifting the wafer was used, the scanning system of the invention is not limited to it. Namely, the invention can be applied to such a method or apparatus as to scan the laser beam two-dimensionally in X- and Y-directions.

When such a fact is considered that scattered light from a recess is not detected if the angle of incidence is made large because then the scattered light from the recess becomes weak, it may become possible to distinguish between a foreign matter, a scratch, or the like on the wafer surface and a recess in a spot form present on the wafer surface by making the angle of incidence large and using a suitable signal detecting circuit, while using only one wavelength. In that case, when the size of a foreign matter becomes very small, it becomes necessary to detect even a weak signal. Then, the signal from a recess also comes to be detected. On the other hand, when the configuration in which signal strengths are compared as described in the foregoing, a foreign matter and a recess can be distinguished even if the size of the foreign matter becomes very small.

According to the embodiment of FIGS. 12–13, the surface inspecting apparatus of a wafer for semiconductor substrates or the like can detect, except small recesses which present no problem in the fabrication of semiconductor integrated circuits, foreign matters attached to the wafer surface or scratch thereon and recesses in a spot form present on the wafer surface with distinction between them. Consequently, waste of material of wafers can be reduced.

What is claimed is:

1. A surface inspection apparatus comprising:
  a light source portion for emitting a light wave of a first wavelength and a light wave of a second wavelength;
  a first irradiating optical system for directing a light beam of a first wavelength onto the surface of an inspected body in a first angle of irradiation;
  a second irradiating optical system for directing a light beam of a second wavelength onto the surface of the inspected body in a second angle of irradiation different from the first angle of irradiation and at the same time said light beam of the first wavelength is directed by the first irradiating optical system;

a first photosensing optical system for sensing in a first photosensing direction scattered light from the surface of the inspected body irradiated by said first irradiating optical system;

a second photosensing optical system for sensing in a second photosensing direction scattered light from the surface of the inspected body irradiated by said second irradiating optical system;

a first photosensing portion for converting the scattered light of the first wavelength sensed by said first photosensing optical system into a first sensed-light signal;

a second photosensing portion for converting the scattered light of the second wavelength sensed by said first photosensing optical system into a second sensed-light signal;

a third photosensing portion for converting the scattered light of the first wavelength sensed by said second photosensing optical system into a third sensed-light signal;

a fourth photosensing portion for converting the scattered light of the second wavelength sensed by said second photosensing optical system into a fourth sensed-light signal;

a displacement portion for displacing said inspected body and the light beams emitted from said irradiating optical systems relative to each other; and a signal processing portion for discriminating inspected objects on the basis of said first to fourth sensed-light optical signals.

2. A surface inspection apparatus according to claim 1, wherein the first angle of said first irradiating optical system is smaller than the second angle of said second irradiating optical system, and a first photosensing angle formed, on the surface of the inspected body, between the first photosensing direction in which said first photosensing optical system senses light and the direction of the regular reflection of light beams directed by said first irradiating optical system or said second irradiating optical system is larger than a second photosensing angle formed between said second photosensing optical system and the direction of the regular reflection.

3. A surface inspection apparatus according to claim 2, wherein said signal processing portion forms a first processed signal on the basis of said first sensed-light signal or third sensed-light signal and a second processed signal on the basis of said second sensed-light signal or fourth sensed-light signal and identifies, as the inspected object, a first inspected object by data included in both of said first processed signal and second processed signal and a second inspected object by data included in only either of said first processed signal and second processed signal.

4. A surface inspection apparatus according to claim 3, further comprising sensitivity setting means capable of changing over sensitivity of each of said first photosensing portion to fourth photosensing portion between a high sensitivity and a low sensitivity, wherein said sensitivity setting means, when said inspected body produces small surface scattering, sets said first photosensing portion and said second photosensing portion at the high sensitivity and sets said third photosensing portion and said fourth photosensing portion at the low sensitivity.

5. A surface inspection apparatus according to claim 3, further comprising sensitivity setting means capable of changing over sensitivity of each of said first photosensing portion to fourth photosensing portion between a high sensitivity and a low sensitivity, wherein said sensitivity setting means, when said inspected body produces great surface scattering, sets said first photosensing portion and said second photosensing portion at the low sensitivity and sets said third photosensing portion and said fourth photosensing portion at the high sensitivity.

6. A surface inspection apparatus according to claim 4, wherein said inspected body is a bare semiconductor wafer and said signal processing portion identifies a foreign matter on the surface of the semiconductor wafer as said first inspected object and identifies a small recess on the surface of the semiconductor wafer as said second inspected object.

7. A surface inspection apparatus according to claim 6, further comprising:

a display portion for displaying either or both of a foreign matter on the surface of the semiconductor wafer identified, by said signal processing portion, as said first inspected object and a small recess on the surface of the semiconductor wafer identified as said second inspected object.

8. A surface inspection apparatus according to claim 6, further comprising a storage portion for storing results of identification made by said signal processing portion, wherein said storage portion is adapted such that, when an inspected object inspected in the past is inspected again, said signal processing portion associates results of identification stored in said storage portion with results of identification obtained in a current inspection.

9. A wafer surface inspecting method comprising the steps of:

focusing light beams emitted from a light source on the surface of a wafer;

sensing scattered light from the focused point with a photoelectric converter while the focused point is scanned; and inspecting foreign matters and flaws on the wafer surface through detection of signals from said photoelectric converter, wherein irradiating light beams of two wavelengths are focused on one and the same point in different angles of incidence and at the same time scattered light beams from the focused point are photoelectrically converted separately for each of the two wavelengths, and discriminating a foreign matter or flaw on the wafer surface and a recess in a spot form existing on the wafer surface from each other by utilizing differences in intensity of the signals.

10. A wafer surface inspecting method according to claim 9, wherein, in sensing scattered light beams of two different wavelengths, a photosensing position is set to be in the same relationship with planes of incidence of the irradiating light beams of the different wavelengths.

11. A wafer surface inspection apparatus comprising:

a light source;

an optical system for focusing light beams from said light source on a wafer surface;

a photosensing portion including a photoelectric converter for sensing scattered light beams from a focused point;

a signal detector for detecting signals from said photosensing portion, wherein said light source is a light source of two different wavelengths and said optical system is adapted to focus light beams of two wavelengths on said focussed point on the wafer surface in different angles of incidence and at the same time; and a discriminating circuit for discriminating between a foreign matter or flaw on the wafer surface and a recess in a spot form existing on the wafer surface by utilizing outputs from said signal detector.

12. A wafer surface inspection apparatus according to claim 11, wherein said photosensing portion for sensing scattered light beams of two different wavelengths is arranged to be in the same relationship with planes of incidence of the irradiating light beams of the different wavelengths.

\* \* \* \* \*